United States Patent
Holweg et al.

(10) Patent No.: US 9,171,245 B2
(45) Date of Patent: Oct. 27, 2015

(54) CHIP ARRANGEMENT, ANALYSIS APPARATUS, RECEIVING CONTAINER, AND RECEIVING CONTAINER SYSTEM

(71) Applicant: Infineon Technologies AG, Neubiberg (DE)

(72) Inventors: Gerald Holweg, Graz (AT); Thomas Herndl, Biedermannsdorf (AT); Guenter Hofer, St. Oswald (AT); Walther Pachler, Graz (AT)

(73) Assignee: INFINEON TECHNOLOGIES AG, Neubiberg (DE)

(*) Notice: Subject to any disclaimer, the term of this patent is extended or adjusted under 35 U.S.C. 154(b) by 0 days.

(21) Appl. No.: 14/468,372

(22) Filed: Aug. 26, 2014

(65) Prior Publication Data

US 2015/0053772 A1    Feb. 26, 2015

(30) Foreign Application Priority Data

Aug. 26, 2013 (DE) .......................... 10 2013 109 221

(51) Int. Cl.
*G06K 19/06* (2006.01)
*G06K 19/077* (2006.01)
*G01N 33/00* (2006.01)

(52) U.S. Cl.
CPC .......... *G06K 19/07794* (2013.01); *G01N 33/00* (2013.01); *G06K 19/07775* (2013.01); *G06K 19/07779* (2013.01)

(58) Field of Classification Search
CPC .......... G06K 5/00; G06K 7/08; G06K 21/00; G06K 19/06; G06K 19/02; G06F 7/00
USPC .......................... 235/492, 380, 375, 451, 487
See application file for complete search history.

(56) References Cited

U.S. PATENT DOCUMENTS

| | | | |
|---|---|---|---|
| 4,526,474 A | 7/1985 | Simon | |
| 6,380,858 B1 | 4/2002 | Yarin et al. | |
| 7,411,508 B2 | 8/2008 | Harazin et al. | |
| 7,466,230 B2 | 12/2008 | Bergsmann et al. | |
| 7,592,914 B2 | 9/2009 | Sakama et al. | |
| 8,237,622 B2 | 8/2012 | Furumura et al. | |
| 2003/0011476 A1 | 1/2003 | Godfrey | |
| 2007/0229228 A1* | 10/2007 | Yamazaki et al. | 340/10.34 |
| 2007/0229281 A1* | 10/2007 | Shionoiri et al. | 340/572.7 |
| 2007/0267431 A1 | 11/2007 | Bergsmann et al. | |
| 2008/0109510 A1 | 5/2008 | Gerlt et al. | |
| 2008/0135446 A1 | 6/2008 | Pohl | |
| 2008/0191332 A1* | 8/2008 | Koyama et al. | 257/679 |

(Continued)

FOREIGN PATENT DOCUMENTS

| AT | 511517 A1 | 12/2012 |
|---|---|---|
| DE | 3335301 A1 | 1/1985 |

(Continued)

*Primary Examiner* — Edwyn Labaze

(57) ABSTRACT

In various embodiments, a chip arrangement includes a first chip having a first antenna which is monolithically integrated in the first chip and is intended to communicate with at least one of an external reader or an external writer; a second chip having a second antenna which is monolithically integrated in the second chip and is intended to communicate with the at least one of the external reader or the external writer; and a booster antenna which is coupled to the first antenna in a first coupling area in order to increase a range of the first antenna and is coupled to the second antenna in a second coupling area in order to increase a range of the second antenna.

18 Claims, 2 Drawing Sheets

(56) References Cited

U.S. PATENT DOCUMENTS

| | | |
|---|---|---|
| 2008/0210701 A1 | 9/2008 | Cooper |
| 2008/0308641 A1* | 12/2008 | Finn .................. 235/492 |
| 2009/0224888 A1 | 9/2009 | Caruana |
| 2009/0289792 A1 | 11/2009 | Potyrailo et al. |
| 2009/0301925 A1 | 12/2009 | Alloro et al. |
| 2010/0066509 A1 | 3/2010 | Okuizumi et al. |
| 2012/0168520 A1* | 7/2012 | Finocchiaro et al. ...... 235/492 |
| 2013/0146671 A1 | 6/2013 | Grieshofer et al. |
| 2014/0084070 A1 | 3/2014 | Pueschner et al. |
| 2014/0145906 A1 | 5/2014 | Kato et al. |
| 2014/0158775 A1 | 6/2014 | Hofer et al. |
| 2014/0218262 A1 | 8/2014 | Tsubaki |
| 2014/0284386 A1 | 9/2014 | Finn et al. |

FOREIGN PATENT DOCUMENTS

| | | |
|---|---|---|
| DE | 19516227 A1 | 11/1996 |
| DE | 10335284 A1 | 2/2005 |
| DE | 102006052007 A1 | 5/2008 |
| DE | 102009031554 A1 | 10/2010 |
| DE | 102009018285 A1 | 11/2010 |
| DE | 102011056323 A1 | 6/2013 |
| DE | 102011056329 A1 | 6/2013 |
| DE | 102013015902 A1 | 3/2014 |
| DE | 102012109359 A1 | 4/2014 |
| JP | 2001101370 A | 4/2001 |
| JP | 2003218624 A | 7/2003 |
| JP | 2005339170 A | 12/2005 |
| JP | 2005339663 A | 12/2005 |
| JP | 2007190140 A | 8/2007 |
| JP | 2007200370 A | 8/2007 |
| JP | 2010035789 A | 2/2010 |
| JP | 2010205345 A | 9/2010 |
| JP | 2011108343 A | 6/2011 |
| JP | 2012108843 A | 6/2012 |
| JP | 2012155787 A | 8/2012 |
| WO | 2009000384 A2 | 12/2008 |
| WO | 2011054000 A1 | 5/2011 |
| WO | 2012103564 A1 | 8/2012 |

* cited by examiner

CHIP ARRANGEMENT, ANALYSIS APPARATUS, RECEIVING CONTAINER, AND RECEIVING CONTAINER SYSTEM

CROSS-REFERENCE TO RELATED APPLICATION

This application claims priority to German Patent Application Serial No. 10 2013 109 221.7, which was filed Aug. 26, 2013, and is incorporated herein by reference in its entirety.

TECHNICAL FIELD

Various embodiments relate generally to a chip arrangement, an analysis apparatus, a receiving container, and a receiving container system.

BACKGROUND

A conventional chip arrangement may have, for example, a chip. The chip may have, for example, an integrated circuit which may have, inter alia, a storage element. The storage element may store data which may have specific information, for example. The chip may have an antenna, for example an antenna monolithically integrated in the chip. The antenna integrated in the chip may have, for example, a conductor loop and/or a coil with one, two or more windings and/or may be referred to as a "coil on module". The chip may be, for example, a communication chip, for example a transponder chip, for example an RFID transponder, for example an RFID tag. The chip arrangement may be an RFID apparatus and/or a chip card, for example.

The antenna may contribute, for example, to an external reader and/or writer being able to communicate with the chip and/or being able to read the data on the chip and/or being able to write the data to the chip, for example being able to store the data in the storage element. In addition, the chip may be inductively supplied with energy via the antenna and the chip can be operated with the aid of the transmitted energy. A long range of the chip during data transmission, for example a read and/or write distance, and/or a range during energy transmission can be achieved, for example, with a booster antenna outside the chip. The booster antenna may be an element of the chip arrangement. The booster antenna is relatively large in comparison with the antenna integrated in the chip. A plurality of chips having a corresponding plurality of booster antennas therefore require considerably more space than a chip having one booster antenna.

SUMMARY

In various embodiments, a chip arrangement includes a first chip having a first antenna which is monolithically integrated in the first chip and is intended to communicate with at least one of an external reader or an external writer; a second chip having a second antenna which is monolithically integrated in the second chip and is intended to communicate with the at least one of the external reader or the external writer; and a booster antenna which is coupled to the first antenna in a first coupling area in order to increase a range of the first antenna and is coupled to the second antenna in a second coupling area in order to increase a range of the second antenna.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

Figure 1:
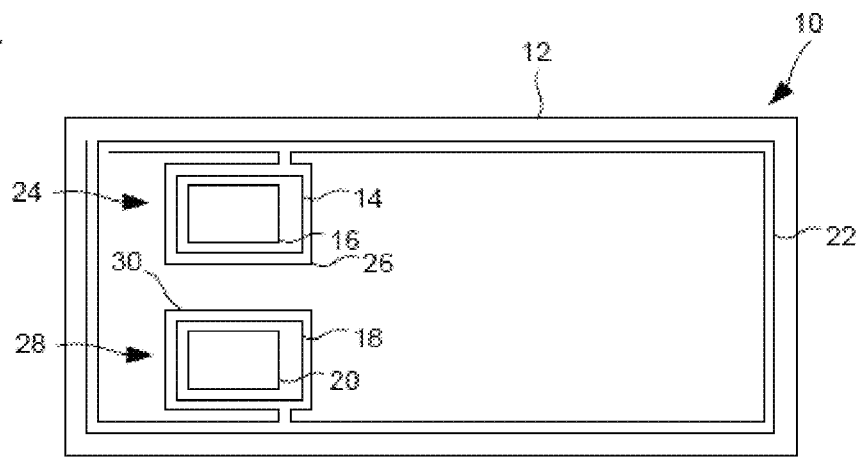
FIG. 1 shows a plan view of an embodiment of a chip arrangement.

The following detailed description refers to the accompanying drawings that show, by way of illustration, specific details and embodiments in which the invention may be practiced.

In the following detailed description, reference is made to the accompanying drawings which form part of this description and show, for the purpose of illustration, specific embodiments in which the invention can be carried out. In this respect, direction terminology, for instance "at the top", "at the bottom", "at the front", "at the rear", "front", "rear", etc., is used with respect to the orientation of the described figure(s). Since components of embodiments can be positioned in a number of different orientations, the direction terminology is used for illustration and is not restrictive in any way. It goes without saying that other embodiments can be used and structural or logical changes can be made without deviating from the scope of protection of the present invention. It goes without saying that the features of the different embodiments described herein can be combined with one another unless specifically indicated otherwise. Therefore, the following detailed description should not be interpreted in a restrictive sense, and the scope of protection of the present invention is defined by the attached claims.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

Within the scope of this description, the terms "linked", "connected" and "coupled" are used to describe both a direct and an indirect link, a direct or indirect connection and direct or indirect coupling. In the figures, identical or similar elements are provided with identical reference symbols if expedient.

Various embodiments provide a chip arrangement which can be designed in a simple, cost-effective and/or space-saving manner and/or can be used to communicate over a long range.

Various embodiments provide an analysis apparatus which can be designed in a simple, cost-effective and/or space-saving manner and/or can be used to communicate over a long range.

Various embodiments provide a receiving container and/or a receiving container system which each enable, in a simple manner, monitored storage of receiving elements, for example simple dosing of medicaments and/or monitoring of the taking of the medicaments.

Various embodiments provide a chip arrangement. The chip arrangement has a first chip having a first antenna which is monolithically integrated in the first chip and is intended to communicate with an external reader and/or writer. The chip arrangement also has a second chip having a second antenna which is monolithically integrated in the second chip and is intended to communicate with the external reader and/or writer. A booster antenna of the chip arrangement is coupled to the first antenna in a first coupling area in order to increase a range of the first antenna and is coupled to the second antenna in a second coupling area in order to increase a range of the second antenna.

The coupling of the first antenna and of the second antenna to the booster antenna makes it possible to use one booster antenna to communicate with two chips. As a result, it is possible to dispense with a second booster antenna for communicating with the second chip. This can contribute to being able to design the chip arrangement in a simple, cost-effective and/or space-saving manner.

The chips can each have one, two or more sensors, for example. If appropriate, the sensors can be monolithically integrated in the corresponding chip. The chips may each have, for example, an energy storage element, for example a battery or a rechargeable battery. If appropriate, the energy storage element may be monolithically integrated in the corresponding chip. The chips may each have, for example, an energy generation module, for example a solar cell or a photodiode. If appropriate, the energy generation module can be monolithically integrated in the corresponding chip.

In various embodiments, the booster antenna is inductively coupled to the first antenna. Alternatively or additionally, the booster antenna is inductively coupled to the second antenna. Alternatively, the first and/or second antenna can be capacitively coupled to the booster antenna. This makes it possible to couple the corresponding antenna to the booster antenna without an electrically conductive and/or galvanic connection to the booster antenna.

In various embodiments, the chip arrangement has a carrier on which the first chip, the second chip and the booster antenna are arranged. The carrier may have plastic, for example, or may be formed therefrom. The carrier may be, for example, an element of a chip card, of a receiving container or of a base body of an analysis apparatus.

In various embodiments, the booster antenna extends around an area in which the first and second chips are arranged. This can contribute to designing the booster antenna to be particularly large and to designing the chip arrangement to nevertheless be space-saving.

In various embodiments, the carrier has a first recess, in which the first chip is arranged, and a second recess, in which the second chip is arranged. The corresponding chip may be permanently connected, for example, to the corresponding recess, for example by means of a bonding agent, for example an adhesive or a solder. If the carrier is the element of the base body of the analysis apparatus, for example, the corresponding chip can be permanently arranged in the corresponding recess. A liquid to be analyzed can then be filled into the corresponding recess and can be analyzed using a sensor of the chip. Alternatively, the corresponding chip can be loosely placed into the corresponding recess. For example, the chip can be physically coupled to a medicament. If the carrier is the element of the receiving container, the medicament with the corresponding chip can be placed into the corresponding recess.

In various embodiments, the first coupling area is formed in the first recess, and the second coupling area is arranged in the second recess. The fact that the coupling area is arranged in the corresponding recess may mean, for example, that the coupling area is arranged in the corresponding recess or that the coupling area is formed adjacent to the corresponding recess or that the coupling area is embedded around an edge of the corresponding recess and/or is embedded in a material of the carrier close to the corresponding recess.

In various embodiments, the booster antenna extends around the first coupling area and around the second coupling area.

In various embodiments, the booster antenna has an electrically conductive material which is printed onto the carrier. In various embodiments, the electrically conductive material may have copper, silver, gold, platinum and/or aluminum or may be formed therefrom.

In various embodiments, the chip arrangement has a first detection antenna which is arranged in the first coupling area, is electrically coupled to the booster antenna and via which the booster antenna is coupled to the first antenna. The chip arrangement also has a second detection antenna which is arranged in the second coupling area, is electrically coupled to the booster antenna and via which the booster antenna is coupled to the second antenna.

In various embodiments, the chip arrangement has more than two chips, for example three, four or more. The chips each have an antenna which is monolithically integrated in the corresponding chip and is intended to communicate with the external reader and/or writer. The booster antenna is coupled to the corresponding antennas in corresponding coupling areas in order to increase the ranges of the corresponding antennas.

Various embodiments provide an analysis apparatus, for example the analysis apparatus mentioned above, for determining at least one property of liquids. The analysis apparatus has the chip arrangement. The first recess is designed to receive a first liquid and the second recess is designed to receive a second liquid. The first chip is arranged in the first recess in such a manner that the first chip can be used to determine the property of the first liquid. The second chip is arranged in the second recess in such a manner that the second chip can be used to determine the property of the second liquid. The first liquid and the second liquid may have identical or different properties, for example chemical properties. The liquids may be blood, for example, and/or the properties may be blood glucose values, for example. The chips may have corresponding sensors for analyzing the liquids, for example. The sensors may be monolithically integrated in the chips, for example.

Various embodiments provide a receiving container having the carrier and the booster antenna. The carrier has the first recess for receiving the first receiving element and at least the second recess for receiving the second receiving element. The booster antenna is formed on the carrier and extends around the first recess and around the second recess. The receiving container can easily enable monitored storage of the receiving elements. The receiving container and the receiving elements form a receiving system. The receiving container may be, for example, a medicament container and/or the receiving elements may be medicaments, for example. If appropriate, dosing and/or taking of medicaments can be easily monitored using the medicament container. The medicament container and the medicaments form a medicament system.

In various embodiments, the receiving container has a first detection antenna and a second detection antenna. The first detection antenna is arranged in the first recess and is coupled to the booster antenna. The second detection antenna is arranged in the second recess and is coupled to the booster antenna. The detection antennas may each be inductively or capacitively coupled to the corresponding antenna, for example. The detection antennas may contribute to improving coupling between the booster antenna and the corresponding antenna of the chip.

Various embodiments provide a receiving container system having the receiving container and the first receiving element and at least the second receiving element. The first receiving element has the first chip with the first antenna and the second receiving element has the second chip with the second antenna. The booster antenna is coupled to the first antenna if the first receiving element with the first chip is arranged in the first recess. The booster antenna is coupled to the second antenna if the second receiving element with the second chip is arranged in the second recess. The receiving container system makes it possible to check whether the receiving elements are arranged in the corresponding recess and therefore in the correct recess, whether the number of receiving elements in the recesses is correct, whether the receiving elements are removed from the recesses at the right time and/or whether the corresponding receiving elements can still be held, in which case the information relating to the receiving elements which is required for this purpose is stored in the form of data in corresponding storage elements on the corresponding chips.

In various embodiments, the receiving container system has an electronic circuit for communicating with the first chip and/or with the second chip. The electronic circuit of the receiving container system communicates with the first chip via the booster antenna and the first antenna and/or communicates with the second chip via the booster antenna and the second antenna. The electronic circuit of the receiving container system can also be coupled to an indication unit, for example an optical and/or acoustic indication unit, so that the correct or incorrect use of the receiving elements, for example the medicaments, can be indicated.

In various embodiments, the electronic circuit of the receiving container system is arranged on or in the carrier of the receiving container.

Various embodiments provide, inter alia, a booster antenna. Various embodiments make it possible to read very small communication modules and/or chips using inductive or capacitive coupling. Various embodiments have a simple structure of the inductive antennas of the chips and/or of the chip capacitance areas, which is why there is no need to carry out optimization processes on the substrate material, for example silicon.

In various embodiments, inductive or capacitive coupling can be used to connect the inductive antennas or chip capacitance areas to a larger antenna structure which enables the conventional use of the corresponding chip as an RFID transponder and/or RFID (radio frequency identification) tag. As a result, a broadband signal, a signal at substantially any frequency in various embodiments, can be fed in and any type of booster antenna can therefore be used.

FIG. 1 shows an embodiment of a chip arrangement 10. The chip arrangement 10 has a first chip 14 having a first antenna 16 which is monolithically integrated in the first chip 14. The first antenna 16 is used for communication between the first chip 14 and an external reader and/or writer. The first chip 14 may form, for example, an RFID transponder and/or an RFID tag. The chip arrangement 10 also has a second chip 18 having a second antenna 20 which is monolithically integrated in the second chip 18. The second antenna 20 is used for communication between the second chip 18 and an external reader and/or writer, for example the external reader and/or writer which communicates with the first chip 14.

Optionally, the chip arrangement 10 may have one or more further chips each having an antenna which is monolithically integrated in the corresponding chip. The corresponding antennas are used for communication between the corresponding chip and an external reader and/or writer, for example the external reader and/or writer which communicates with the first chip 14.

The chip arrangement 10 has a booster antenna 22. The booster antenna 22 is coupled to the first antenna 16 and to the second antenna 20. The booster antenna 22 may be coupled to the first antenna 16 of the first chip 14 in a first coupling area 24, for example. The booster antenna 22 may be coupled to the second antenna 20 of the second chip 18 in a second coupling area 28, for example. For example, the booster antenna 22 may be inductively coupled to the first antenna 16 and/or to the second antenna 20. Alternatively, the first chip 14 and/or the second chip 18 may each have a capacitor with corresponding capacitor plates, with the result that capacitive coupling to the booster antenna 22 is possible. The booster antenna 22 is used to increase the range of the first antenna 16 and/or the range of the second antenna 20.

Optionally, the chips 14, 18 may each have an energy storage element, for example a battery and/or a rechargeable battery, an energy generation module, for example a photodiode and/or a solar cell, for example for electrically charging the energy storage element, and/or a sensor. The sensor may be set up, for example, to record a temperature, a pressure or a proportion of a substance in a liquid or gas.

The two chips 14, 18 use the one common booster antenna 22 to communicate with the external reader and/or writer. The external reader and/or writer may be an RFID reader and/or writer, for example. The chip arrangement 10 may be part of a chip card, of a receiving container or of an analysis apparatus, for example.

The chip arrangement 10 may have, for example, a carrier 12 on which the first chip 14 and the second chip 18 can be arranged. Alternatively or additionally, the booster antenna 22 may be arranged on the carrier 12. The booster antenna 22 may have, for example, an electrically conductive material, for example copper, silver, gold, platinum and/or aluminum, or an alloy having one or more of said materials. The electrically conductive material of the booster antenna 22 may be formed, for example, on the carrier 12 by virtue of the electrically conductive material being printed onto the carrier 12, for example by means of blade coating, screen printing or in an inkjet printing method.

A first detection antenna 26, for example, may be formed in the first coupling area 24. A second detection antenna 30, for example, may be formed in the second coupling area 28. The first detection antenna 26 and the second detection antenna 30 may each be electrically and/or galvanically coupled to the booster antenna 22. Alternatively, the detection antennas 26, 30 may each be inductively coupled to the booster antenna 22. The first detection antenna 26 is used for communication between the first antenna 16 and the booster antenna 22. The second detection antenna 30 is used for communication between the second antenna 20 and the booster antenna 22. In FIG. 1, the detection antennas 26, 30 are in the form of a coil and have only one winding each. Alternatively, however, the detection antennas 26, 30 may each also have two, three or more windings.

Clearly, the booster antenna 22 may be a resonant circuit. In the latter, a large conductor loop can be used to inductively couple in energy. In order to achieve a so-called booster effect, a small respective part of the conductor loop, for example the first or second detection antenna 26, 30, may be formed for each chip 14, 18 in such a manner that said part substantially surrounds the corresponding chip 14, 18. The detection antennas 26, 30 are used to form inductive coupling, in this case to the antennas 16, 20, with the result that it is possible to communicate with the corresponding chip 14, 18 using this inductive coupling. Very good coupling is achieved as a result of the geometrical proximity of the antennas 16, 20 and a respective part of the conductor loop, that is to say the corresponding detection antenna 26, 30. The following generally applies: the more similar and the closer the conductor loops are to one another, the better their inductive coupling.

For example, the booster antenna 22 may be formed using a resonant circuit which, on the one hand, provides first inductive coupling to the external reader and/or writer and, on the other hand, provides second inductive coupling to one of the antennas 16, 20 in each case. The majority of the conductor loop may have a first inductor having a first (large) inductance, a capacitor and a non-reactive resistor and provides inductive coupling to the external reader and/or writer. The smaller part of the conductor loop, that is to say one of the detection antennas 26, 30, has a second inductor having a second inductance and provides inductive coupling to the corresponding antenna 16, 20.

In the case of a capacitively designed chip 14, 18, the chip 14, 18 may be arranged between two parts of the booster antenna 22 and may be capacitively coupled to the latter. The booster antenna can therefore clearly surround the chip 14, 18 and a series resonant circuit, for example, is formed, for example an RFID (radio frequency identification) series resonant circuit.

Each of the chips 14, 18 may have a chip substrate, for example a wafer substrate. The chip substrate may be produced from one or more semiconductor materials, for example silicon, germanium, one or more semiconductor materials from main groups III to V or the like, or from one or more polymers, although other suitable materials can likewise be used in other embodiments. In various embodiments, the chip substrate may be produced from silicon (doped or undoped); in alternative embodiments, the chip substrate may be a silicon on insulator (SOI) substrate. In other embodiments, any other suitable semiconductor material may be provided for the chip substrate, for example a semiconductor composite material, for example gallium arsenide (GaAs), indium phosphide (InP), or else any suitable ternary or quaternary semiconductor composite material, for example indium gallium arsenide (InGaAs).

A wiring structure (not illustrated) having a metallization plane or a plurality of metallization planes may be applied to the chip substrate, in which case a so-called intermediate dielectric (for example an oxide, for example silicon oxide, a nitride, for example silicon nitride, or a low-k dielectric or a high-k dielectric) can be provided between the metallization planes. The plurality of metallization planes can be connected to one another in an electrically conductive manner using one or more contact holes. A rectifier circuit (not illustrated) (for example implemented in the form of a full-bridge circuit or half-bridge circuit), for example, may be formed in the chip substrate (alternatively, however, also (completely or partially) in the wiring structure). The rectifier circuit may also be a rectifier circuit which is set up to rectify (generally to process) broadband signals, in other words signals over a wide frequency range. The wiring structure and/or the rectifier circuit may be part of one or more electronic circuits of the corresponding chip 14, 18. In various embodiments, the electronic circuit of one of the chips 14, 18 may be at least partially formed in the chip substrate of the corresponding chip 14, 18.

The rectifier circuit may be set up to receive an electric field which is supplied from the outside, for example using the external reader and/or writer, and is picked up (in other words received) using the corresponding antenna 16, 20 or using a corresponding capacitor (not illustrated) and to rectify the AC voltage, which is therefore received, into a DC voltage. The rectified voltage can be provided at an output of the rectifier circuit.

The rectifier circuit may be set up to process signals in a frequency range of at least 25% relative to a predefined carrier frequency, for example in a frequency range of at least 30%, for example of at least 35%, for example of at least 40%, for example of at least 45%, for example of at least 50%, for example of at least 55%, for example of at least 60%, for example of at least 65%, for example of at least 70%, for example of at least 75%, for example of at least 80%, for example of at least 85%, for example of at least 90%, for example of at least 95%, for example of at least 100% or more. The carrier frequency may be in a range of approximately 13.56 MHz (HF standard) or of approximately 433 MHz or of approximately 868 MHz or of approximately 2.4 GHz (UHF standard). The signal at the carrier frequency can be used, for example, to supply energy to the corresponding chip 14, 18, and a signal modulated onto the carrier frequency can be used to (bidirectionally) communicate with the chip 14, 18, for example by means of load modulation.

In various embodiments, the rectifier circuit may be set up to process signals in a frequency range of greater than 100 MHz (for example of greater than 200 MHz, 300 MHz, 400 MHz, 500 MHz, 600 MHz, 700 MHz, 800 MHz, 900 MHz, 1 GHz, 1.5 GHz, 2 GHz or even greater) around a carrier frequency (naturally dependent on the carrier frequency in each case), for example in a frequency direction (for example a frequency range greater or less than the carrier frequency), or in both frequency directions (for example a frequency range greater and less than the carrier frequency) starting from the carrier frequency.

The rectifier circuit may be set up in such a manner that it does not have any AC coupling and begins to operate from 0 Hz, and it may be set up to process signals at a frequency up to a maximum switching frequency of the transistors (for example metal oxide semiconductor (MOS) transistors, for example PMOS transistors and/or NMOS transistors) of the rectifier circuit.

Figure 2:
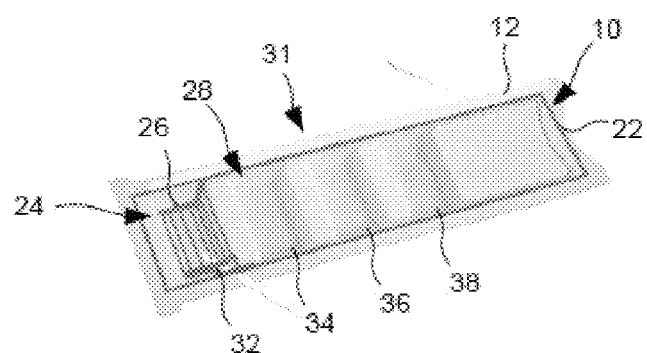
FIG. 2 shows a perspective view of an embodiment of a receiving container.

FIG. 2 shows an embodiment of the chip arrangement 10, in which the chip arrangement 10 is in the form of an element of a receiving container 31, for example. The receiving container 31 has the carrier 12. A first recess 32, a second recess 34, a third recess 36 and a fourth recess 38 may be formed in the carrier 12, for example. Furthermore, the receiving container 31 may have a cover (not illustrated in FIG. 2) which can be used to selectively close the recesses 32 to 38, for example. The receiving container 31 may be used as an apparatus for sorting letters or as a medicament container.

The booster antenna 22 may extend, for example, around an outer edge of the carrier 12 of the receiving container 31. For example, the booster antenna 22 may extend around the recess 32 to 38.

The first detection antenna 26, for example, may be formed in the first recess 32. The fact that the first detection antenna 26 is arranged in the first recess 32 may mean, for example, that the first detection antenna is arranged in the first recess 32 or that the first detection antenna 26 is formed adjacent to the first recess 32 or that the first detection antenna 26 is embedded close to the first recess 32, for example around an edge of the first recess 32, and/or is embedded in a material of the carrier 12 close to the first recess 32. The corresponding second detection antenna 30 (not illustrated in FIG. 2) or a third detection antenna (not illustrated) and/or a fourth detection antenna (not illustrated) may be formed close to the second recess 34, the third recess 36 and/or the fourth recess 38.

The recesses 32 to 38 may be used, for example, to receive individual receiving elements, for example letters or medicaments, for example tablets and/or pills. For example, dosing of the medicaments can be improved and/or facilitated with the aid of the receiving container 31. For example, the medicaments which have to be taken in the morning can be arranged in the first recess 32, the medicaments which have to be taken at midday can be arranged in the second recess 34, the medicaments which have to be taken in the evening can be arranged in the third recess 36 and the medicaments which have to be taken at night can be arranged in the fourth recess 38.

The receiving elements which can be arranged in the recesses 32 to 38 may have, for example, chips, in particular RFID transponder chips, for example the first chip 14 and/or the second chip 18. For example, a first medicament can have the first chip 14 and a second medicament can have the second chip 18. If a medicament, for example the first medicament with the first chip 14, is arranged in the first recess 32, an external reader and/or writer can communicate with the first chip 14 via the booster antenna 22, the first detection antenna 26 and the first antenna 16 of the chip 14. For example, the external reader and/or writer can therefore determine whether the first medicament is actually arranged in the first recess 32. If the first medicament is arranged in the first recess 32, the external reader and/or writer can detect this and can read, for example, data stored on the first chip 14, for example in a storage element (not illustrated) of the first chip 14.

The data may include, for example, information which may relate to the first chip 14 and/or to the first medicament, for example. The information may relate to a prescribed dose, an expiry date and/or ingredients of the first medicament, for example. In this manner, the external reader and/or writer can be used to check whether the correct medicaments are arranged in the correct recess and/or whether the correct medicaments are removed at the correct time and/or whether the correct number of medicaments is arranged in the recesses and is then removed again at the correct time. If the receiving elements are letters, the data may have a sender address and/or a recipient address, for example.

The first and second medicaments may be different medicaments, for example. Alternatively, the first medicament and the second medicament may be the same medicament, for example different pills and/or tablets with the same active ingredients.

The receiving container and the receiving elements form a receiving container system. The medicament container and the medicaments form a medicament system.

Figure 3:
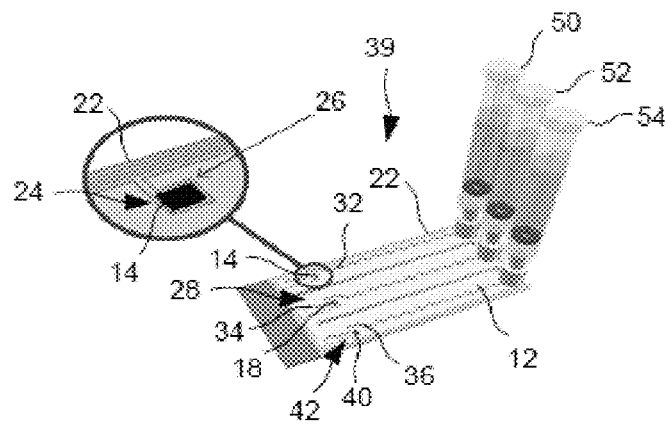
FIG. 3 shows a perspective view of an embodiment of an analysis apparatus.

FIG. 3 shows an embodiment of an analysis apparatus 39 for determining at least one property of liquids. The analysis apparatus 39 may have the chip arrangement 10, for example. In various embodiments, the analysis apparatus 39 may have the first chip 14, the second chip 18 and a third chip 40.

Accordingly, the analysis apparatus 39 may have the first coupling area 24, the second coupling area 28 and a third coupling area 42 for coupling the booster antenna 22 to the third chip 40. The chips 14, 18, 40 may be coupled to the one booster antenna 22 in the corresponding coupling areas 24, 28, 42.

In addition, the analysis apparatus 39 may have the carrier 12 in which the first recess 32, the second recess 34 and the third recess 36 are formed. The carrier 12 may form, for example, a base body of the analysis apparatus 39. The booster antenna 22 may extend, for example, around the recesses 32 to 34, for example along an edge of the carrier 12 of the analysis apparatus 39.

The analysis apparatus 39 has a first container 50, a second container 52 and a third container 54. The first container 50 may be arranged, for example, above the first recess 32, the second container 52 may be arranged, for example, above the second recess 34 and/or the third container 54 may be arranged, for example, above the third recess 36.

The first chip 14, for example, can be permanently arranged in the first recess 32. The second chip 18, for example, can be permanently arranged in the second recess 34 and/or the third chip 40, for example, can be permanently arranged in the third recess 36. The chips 14, 18, 40 can be permanently coupled, for example, to the carrier 12; for example, the chips 14, 18, 40 can be firmly stuck to the carrier 12, to be precise in the corresponding recesses 32, 34, 36. The chips 14, 18, 40 may each have, for example, a sensor for recording a property of one or more liquids. For example, a content of a predefined substance in a liquid can be detected with the aid of the corresponding sensor. A blood glucose content in the blood can be determined using one of the sensors in each case, for example, in which case blood is then the liquid and the blood glucose content is the property of the liquid.

The liquid or two, three or more liquids can be arranged or poured into the first container 50, the second container 52 and the third container 54. The liquids in the containers 50 to 54 can be passed to the corresponding chips 14, 18, 40 via the corresponding recesses 32 to 34 and can be analyzed there by means of the chips 14, 18, 40.

FIG. 4 to FIG. 7 show various embodiments of the booster antenna 22. The embodiments according to FIG. 4 to FIG. 7 each illustrate only the first coupling area 24 and the first chip 14. In actual fact, however, the second chip 18 and the second coupling area 28 and optionally further chips and accordingly also corresponding further coupling areas may be formed and/or arranged.

Figure 4:
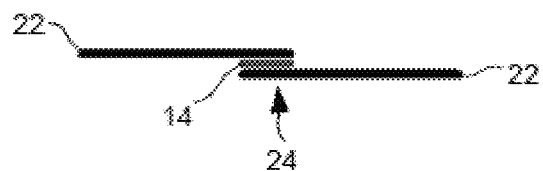
FIG. 4 shows an embodiment of a booster antenna.

FIG. 4 shows an embodiment of the booster antenna 22, in which the latter is in the form of an ultra-high frequency (UHF) antenna, for example a dipole, and is capacitively coupled to the first chip 14.

Figure 5:
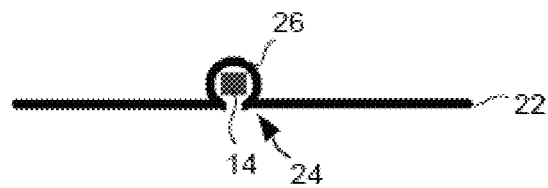
FIG. 5 shows an embodiment of a booster antenna.

FIG. 5 shows an embodiment of the booster antenna 22, in which the booster antenna 22 is in the form of a UHF antenna, for example a dipole, and is coupled to the first chip 14 inductively, for example via the first detection antenna 26.

Figure 6:
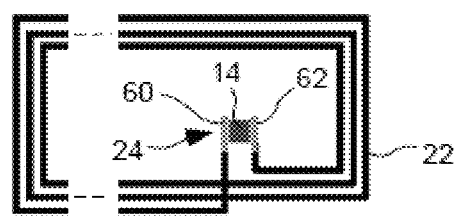
FIG. 6 shows an embodiment of a booster antenna.

FIG. 6 shows an embodiment of the booster antenna 22, in which the booster antenna 22 is in the form of a high-frequency (HF) antenna, for example a coil, and is capacitively coupled to the first chip 14. For this purpose, the booster antenna 22 may have a capacitor having a first capacitor plate 60 and a second capacitor plate 62, between which the first chip 14 is arranged.

Figure 7:
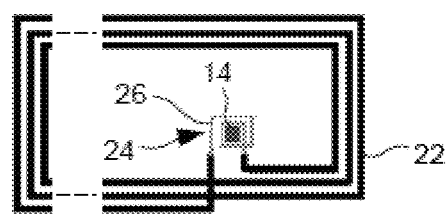
FIG. 7 shows an embodiment of a booster antenna.

FIG. 7 shows an embodiment of the booster antenna 22, in which the booster antenna 22 is in the form of an HF antenna, for example a coil, and is coupled to the first chip 14 inductively, for example via the first detection antenna 26.

The invention is not restricted to the embodiments stated. For example, the various embodiments can be combined with one another. For example, the basic principles of the booster antenna 22 shown in FIG. 4 to FIG. 7 can be applied to the chip arrangement 10 according to FIG. 1, to the receiving container 31 according to FIG. 2 and/or to the analysis apparatus 39 according to FIG. 3. Furthermore, the chip arrangement 10 according to FIG. 1 may have the recess 32, 34, 36 and/or 38 according to FIG. 2. Furthermore, the embodiments shown in FIG. 1 to FIG. 3 may have two, three or more chips and/or corresponding coupling areas and/or corresponding recesses and/or corresponding detection antennas. Furthermore, the detection antennas 26, 30 may be provided in all embodiments and/or may have one, two, three or more windings in all embodiments. Furthermore, in all embodiments, the booster antenna 22 may have one, two, three or more windings outside the detection antennas 26, 30. Furthermore, more than two chips, for example three, four or more, may be arranged and each have an antenna which is monolithically integrated in the corresponding chip and is intended to communicate with the external reader and/or writer. If necessary, the booster antenna is coupled to the corresponding antennas in corresponding coupling areas in order to increase the ranges of the corresponding antennas.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A chip arrangement, comprising:
    a first chip having a first antenna which is monolithically integrated in the first chip and is intended to communicate with at least one of an external reader or an external writer;
    a second chip having a second antenna which is monolithically integrated in the second chip and is intended to communicate with the at least one of the external reader or the external writer;
    a booster antenna which is coupled to the first antenna in a first coupling area in order to increase a range of the first antenna and is coupled to the second antenna in a second coupling area in order to increase a range of the second antenna;
    a first detection antenna which is arranged in the first coupling area, is electrically coupled to the booster antenna and via which the booster antenna is coupled to the first antenna; and
    a second detection antenna which is arranged in the second coupling area, is electrically coupled to the booster antenna and via which the booster antenna is coupled to the second antenna; and
    wherein the first coupling area is separate from second coupling area.

2. The chip arrangement of claim 1,
    wherein the booster antenna is inductively coupled to at least one of the first antenna or the second antenna.

3. The chip arrangement of claim 1, further comprising:
    a carrier on which the first chip, the second chip and the booster antenna are arranged.

4. The chip arrangement of claim 3,
    wherein the booster antenna extends around an area in which the first and second chips are arranged.

5. The chip arrangement of claim 4,
    wherein the carrier has a first recess; in which the first chip is arranged, and a second recess, in which the second chip is arranged.

6. The chip arrangement of claim 5,
    wherein the first coupling area is formed in the first recess; and
    wherein the second coupling area is arranged in the second recess.

7. The chip arrangement of claim 3,
    wherein the booster antenna extends around the first coupling area and around the second coupling area.

8. The chip arrangement of claim 3,
    wherein the booster antenna has an electrically conductive material which is printed onto the carrier.

9. The chip arrangement of claim 1,
    which has more than two chips each having an antenna which is monolithically integrated in the corresponding chip and is intended to communicate with the at least one of the external reader or the external writer, the booster antenna being coupled to the corresponding antennas in corresponding coupling areas in order to increase the ranges of the corresponding antennas.

10. An analysis apparatus for determining at least one property of liquids, the analysis apparatus comprising:
    a chip arrangement, comprising:
        a first chip having a first antenna which is monolithically integrated in the first chip and is intended to communicate with at least one of an external reader or an external writer;
        a second chip having a second antenna which is monolithically integrated in the second chip and is intended to communicate with the at least one of the external reader or the external writer;
        a booster antenna which is coupled to the first antenna in a first coupling area in order to increase a range of the first antenna and is coupled to the second antenna in a second coupling area in order to increase a range of the second antenna;
        a first detection antenna which is arranged in a first recess and coupled to the booster antenna; and
        a second detection antenna which is arranged in a second recess and coupled to the booster antenna;
    wherein the first recess is designed to receive a first liquid; and
    wherein the second recess is designed to receive a second liquid; and
    wherein the first chip is arranged in the first recess in such a manner that the first chip can be used to determine the property of the first liquid, and the second chip is arranged in the second recess in such a manner that the second chip can be used to determine the property of the second liquid.

11. The analysis apparatus for determining at least one property of liquids of claim 10,
    wherein the booster antenna is coupled to the first antenna at least via the first detection antenna and the booster antenna is coupled to the second antenna at least via the second detection antenna.

12. The analysis apparatus for determining at least one property of liquids of claim 11,
    wherein the booster antenna is coupled to the first antenna in a first coupling area and the first detection antenna is arranged in the first coupling area,
    and wherein the booster antenna is coupled to the second antenna in a second coupling area and the second detection antenna is arranged in the second coupling area.

13. A receiving container, comprising:
a carrier which has a first recess for receiving a first receiving element and at least one second recess for receiving a second receiving element;
a booster antenna which is formed on the carrier and extends around the first recess and around the second recess;
a first detection antenna which is arranged in the first recess and is coupled to the booster antenna; and
a second detection antenna which is arranged in the second recess and is coupled to the booster antenna, and
wherein the first recess comprises a first coupling area and the second recess comprises a second coupling area, wherein the first coupling area is separate from second coupling area.

14. A receiving container system, comprising:
a receiving container, comprising:
- a carrier which has a first recess for receiving a first receiving element and at least one second recess for receiving a second receiving element; and
- a booster antenna which is formed on the carrier and extends around the first recess and around the second recess; and
the first receiving element;
at least the second receiving element;
wherein the first receiving element has a first chip with a first antenna; and
wherein the second receiving element has a second chip with a second antenna;
wherein the booster antenna is coupled to the first antenna if the first receiving element with the first chip is arranged in the first recess;
wherein the booster antenna is coupled to the second antenna if the second receiving element with the second chip is arranged in the second recess;
a first detection antenna which is arranged in the first recess and coupled to the booster antenna; and
a second detection antenna which is arranged in the second recess and is coupled to the booster antenna; and
wherein the first coupling area is separate from second coupling area.

15. The receiving container system of claim 14,
which has an electronic circuit for communicating at least one of with the first chip or with the second chip, the electronic circuit at least one of communicating with the first chip via the booster antenna and the first antenna or communicating with the second chip via the booster antenna and the second antenna.

16. The receiving container system of claim 15,
wherein the electronic circuit is arranged on or in the carrier of the receiving container.

17. The receiving container system of claim 14,
wherein the booster antenna is coupled to the first antenna at least via the first detection antenna and the booster antenna is coupled to the second antenna at least via the second detection antenna.

18. The receiving container system of claim 17,
wherein the booster antenna is coupled to the first antenna in a first coupling area and the first detection antenna is arranged in the first coupling area,
and wherein the booster antenna is coupled to the second antenna in a second coupling area and the second detection antenna is arranged in the second coupling area.

\* \* \* \* \*